United States Patent [19]

Berg

[11] Patent Number: 4,875,247

[45] Date of Patent: Oct. 24, 1989

[54] DISPOSABLE TOOTH CLEANING & POLISHING APPARATUS

[76] Inventor: Skip Berg, P. O. Drawer 725, Venice, Fla. 34282

[21] Appl. No.: 371,689

[22] Filed: Jun. 20, 1989

Related U.S. Application Data

[63] Continuation of Ser. No. 83,028, Aug. 7, 1987, abandoned.

[51] Int. Cl.$^4$ ............................................. A61C 17/00
[52] U.S. Cl. ............................... 15/104.94; 15/209 R; 15/227
[58] Field of Search ........... 15/104.94, 104.93, 209 R, 15/210 R, 227; 428/152–154; 401/7, 8

[56] References Cited

U.S. PATENT DOCUMENTS

| | | | |
|---|---|---|---|
| 3,616,157 | 10/1971 | Smith | 15/209 R |
| 3,902,509 | 9/1975 | Tundermann et al. | 15/227 |
| 3,965,519 | 6/1976 | Hermann | 15/209 R |

FOREIGN PATENT DOCUMENTS

| | | | |
|---|---|---|---|
| 360066 | 11/1931 | United Kingdom | 15/209 R |

Primary Examiner—Edward L. Roberts

[57] ABSTRACT

A disposable tooth cleaning and polishing product for manually cleaning teeth comprising a sheet of thin, flexible material such as paper, cloth or synthetic foam material which may also be formed and contoured. The material is substantially insoluble in water and oral cavity juices and has at least one surface with sufficient surface texture to remove plaque, food residue and film, and oral cavity acids from teeth surfaces by manually rubbing the material with finger pressure against the teeth while also being sufficiently soft and pliable so as to avoid injuring or abrading the gums. The formed, flexible material may have various embodiments each adapted to fit over the end of the user's finger for enhanced retention for rubbing against the teeth. The flexible sheet may also include releasable adhesion means on one surface for attachment to the fingertip and may also be retained in place against the fingertip by a ring over the finger and sheet fitted to the finger's first knuckle. A flexible sheet may be provided individually, packaged for dispensing, or in roll form perforated for convenient separation.

13 Claims, 2 Drawing Sheets

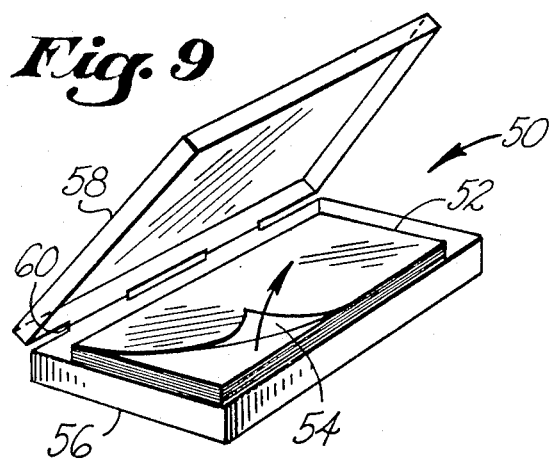
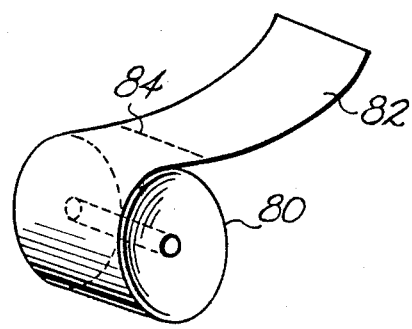
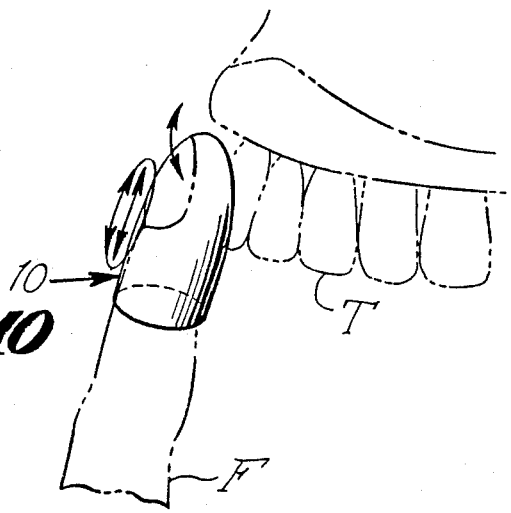
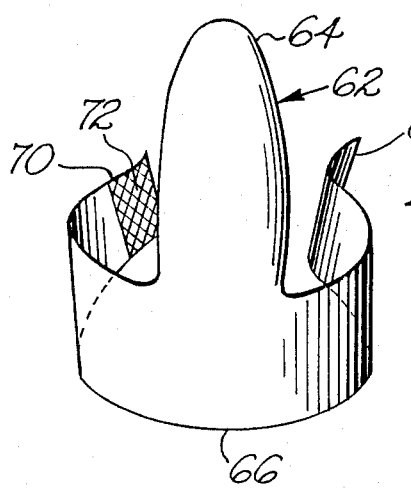
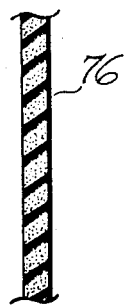
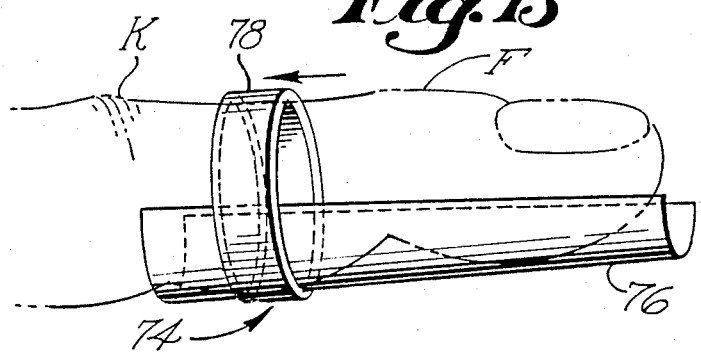

DISPOSABLE TOOTH CLEANING & POLISHING APPARATUS

This is a continuation of co-pending application Ser. No. 07/083,028 filed on Aug. 7, 1987 now abandoned.

BACKGROUND OF THE INVENTION

This invention relates generally to dental products and particularly to a disposable tooth cleaning and polishing product usable after eating and at any convenient time or location during the day for removing film and food deposits and oral cavity juices from the teeth to help reduce plaque build-up and to freshen the user's breath.

Many products such as tooth brushes and pressurized pulsating water devices are available and well-known for cleaning the teeth at specific times of the day in the privacy of one's own home. However, because plaque, food particles and oral acids and the like build up on teeth continuously during the day, and particularly after meals, many individuals more conscientious about maintaining good dental hygiene, prefer to engage in some form of teeth cleaning periodically during the day in conditions and circumstances which do not lend themselves conveniently to more private and personal forms of dental hygiene.

Several well-known techniques for attempting to affect dental hygiene during the day are known to applicant. One obvious method is simply the chewing of variously commercially available types of gum, some sugared, and some artifically sweetened, to reduce detrimental effects upon cavity formation and general oral hygiene. Another well-known form of mouth freshing resides in simply rinsing the mouth with a commercially available mouthwash, some flavored, some including medicinal and antibacterial components.

Another invention known to applicant is disclosed in U.S. Pat. No. 1,421,911 to Cohen which discloses a tooth cleaning device having an elongated handle which is interengageable into a cylindrically shaped tooth cleaning roll which comprises an elongated strip of two-part material having cotton as a base or carrier inherently attached to a layer of thin facing of non-absorbent cotton. The roll, when used for cleaning teeth, is impregnated with a dentifrice into the cotton layer. Another prior art invention known to applicant is disclosed in U.S. Pat. No. 4,554,154 to White which discloses a dental product in the form of a chewable plastic embodied in strip or foam capsule or cloth which is intended to be partially masticated and then vigorously rubbed against the tooth surfaces to effect cleaning.

The present invention discloses a much simpler and less expensive to manufacture invention for effecting convenient and unobtrusive cleaning of the teeth surfaces at virtually any period during the day, even at a restaurant table after enjoying a meal. Additional uses of the present invention are for cleaning the teeth of patients after oral surgery and for use by attendants of geriatric patients who can no longer clean their own teeth. As provided by the present invention, the user may simply, by holding one of the various forms of the invention, vigorously rub each of the tooth surfaces with the appropriate surface thereagainst until virtually all of the tooth surface residue has been rubbed free and collected on the surface of the invention. Thereafter, disposal is effected in a manner similar to disposing of a small piece of paper. By the various embodiments, the user may be provided with a broad range of choice in the structure which he prefers to utilize, whether it be by simple releasable adhesion means to his fingertip or alternately held thusly by a separate finger ring which may enhance the novelty and ornamentality of the procedure.

BRIEF SUMMARY OF THE INVENTION

This invention is directed to a disposable tooth cleaning and polishing device for manually cleaning teeth comprising a sheet of thin, flexible material such as paper, cloth or synthetic foam material which may also be formed or contoured and which is sufficiently soft and pliable so as to avoid abraiding the gums. The material is substantially insoluble in water and oral cavity juices and has at least one surface with sufficient surface texture to remove plaque, food residue and film, and oral cavity acids from teeth surfaces by manually rubbing the material with finger pressure against the teeth. The formed or contoured flexible material may have various embodiments each adapted to fit over the end of the user's finger for enhanced retention and more vigorous rubbing against the teeth. The flexible sheet may also include releasable adhesion means on one surface for attachment to a finger and may also be retained in place against the finger end by a ring over the finger and sheet fitted to the finger's first knuckle. A flexible sheet may be provided individually, packaged for dispensing, or provided in roll form perforated for convenient separation of single portions for use.

It is therefore an object of this invention to provide a convenient, disposable and inexpensive dental product for a convenient and unobtrusive manual cleaning of the teeth and stimulation of the gingival tissue at any time during normal daily activity and to facilitate cleaning the teeth of those who are unable to do so themselves.

It is another object to provide the above invention in various forms to enhance its marketability and versatility.

It is yet another object to provide the above invention which may be packaged in various convenient forms for carrying and dispensing.

It is yet another object of the present invention to utilize various inexpensive and commercially available sheet materials in manufacturing the invention.

In accordance with these and other objects which will become apparent hereinafter, the instant invention will now be described with reference to the accompanying drawings in which:

BRIEF DESCRIPTION OF THE DRAWINGS

FIG. 9 is a perspective view of one embodiment of the invention in containerized form for convenient dispensing.

FIG. 10 is a perspective view of the invention shown in FIG. 1 in use.

FIG. 11 is a perspective view of yet another embodiment of the invention.

FIG. 12 is a partial side elvation section view of yet another embodiment of the invention.

FIG. 13 is a perspective view of yet another embodiment of the invention installed ready for use.

FIG. 14 is a perspective view of another embodiment of the packaging of the invention.

DETAILED DESCRIPTION OF THE INVENTION

Figure 1:
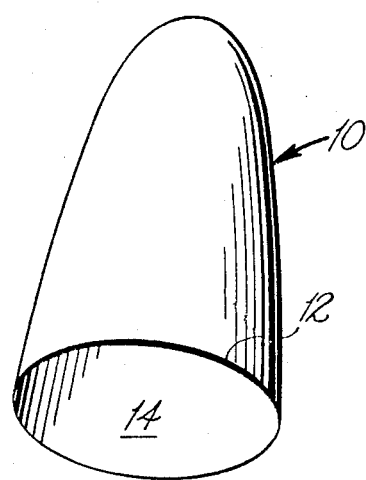
FIG. 1 is a perspective view of one embodiment of the invention.

Referring now to the drawings, and particularly to FIGS. 1 and 10, one embodiment of the invention is shown generally at 10 formed of a continuous sheet of thin, flexible paper material contoured and formed to have opening 14 formed by continuous margin 12 into which opening 14 a user's finger F may be inserted as shown in FIG. 10. Thereafter, by vigorously rubbing the device 10 in the various directions of the arrows, the surface of the teeth T are thereby mechanically cleaned. Any residue removed from the teeth T adheres to the outer surface of the device 10 which is disposed of after one-time use.

Figure 2:
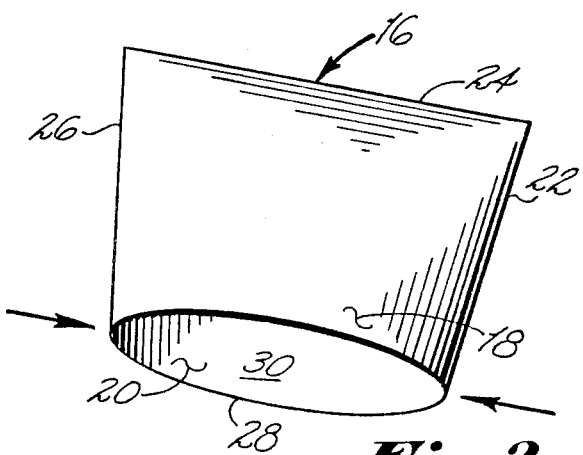
FIG. 2 is a perspective view of another embodiment of the invention.

Referring now to FIG. 2, another embodiment of the invention is shown generally at 16 and includes two rectangularly shaped sheets of thin, flexible paper 18 and 20 which are connected together along three of their margins 22, 24 and 26. By this arrangement then, the user may, by hand, squeeze the opposing connected margins 22 and 26 together in the direction of the arrows, thereby forming opening 30 along the unconnected margin 28 into which the end of the user's finger may be inserted for use as previously described with respect to FIG. 10.

Figure 4:
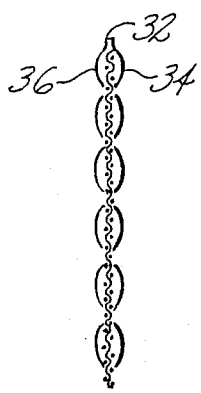
FIG. 4 is a section view in the direction of arrows 4—4 in FIG. 3.
Figure 3:
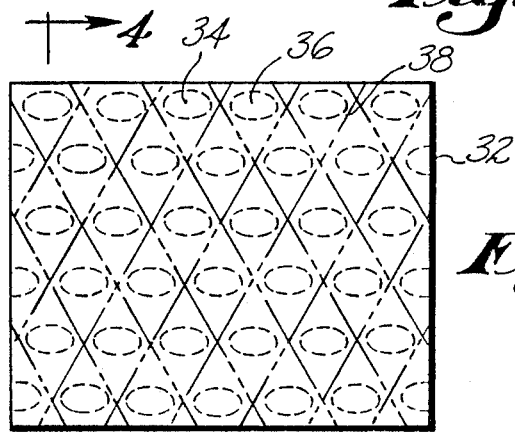
FIG. 3 is a front elevation view of yet another embodiment of the invention.

Referring now to FIGS. 3 and 4, the preferred embodiment of the invention is shown at 32 and is formed of a single generally rectangular shaped sheet of flexible paper product having opposing dimples 34 and 36 extending in either direction from the central cross sectional plane of the paper sheet 32. This dimpling of the otherwise thin flexible sheet of paper enhances the formability of the surface against the user's teeth to enhance the cleaning and polishing ability of the sheet 32.

Figure 5:
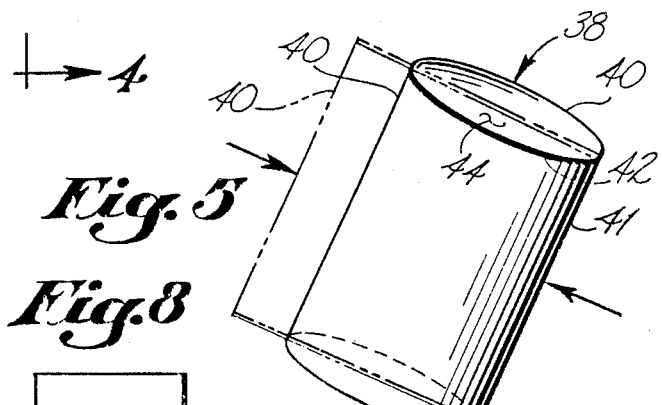
FIG. 5 is a perspective view of yet another embodiment of the invention.

Referring now to FIG. 5, an alternate embodiment to that shown in FIG. 2 is depicted generally at 38 and includes two thin, flexible sheets of paper 40 and 42 interconnected only along their opposing margins 40 and 41 by well-known means. By this arrangement then, again the user may squeeze the margins 40 and 41 together by finger pressure in the direction of the arrows, thus creating opening 44 into and through which the end of the finger may be inserted for use as previously described.

Figures 6, 7, 8:
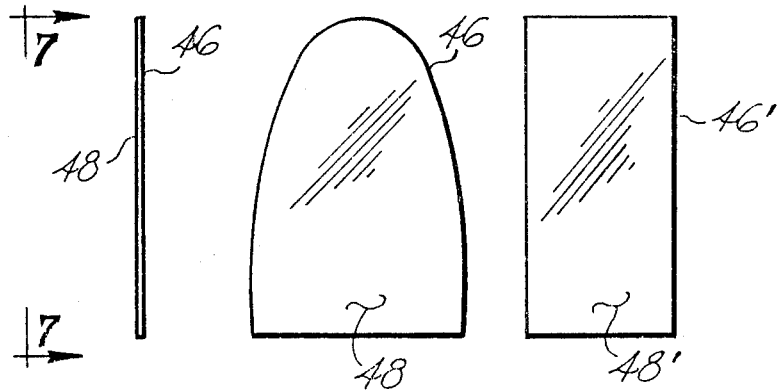
FIG. 6 is a side elevation view of yet another embodiment of the invention.
FIG. 7 is a view in the direction of arrows 7–7 in FIG. 6.
FIG. 8 is a view similar to FIG. 7 except having a rectangular front elevation profile.

Referring to FIGS. 6, 7 and 8, this embodiment of the invention includes either sheet 46 or 46' formed again of thin, flexible paper stock and also having a releasable adhesive layer 48 or 48' disposed on one surface thereof. The adhesive layer 48 is generally of relative low adhesive strength so that this embodiment of the invention may be provided in tablet form having a plurality of these sheets 46 or 46' attached one to another for easy separation one at a time. The user then simply adheres the releasable adhesive surface 48 or 48' against his tip for manual rubbing same against tooth surfaces as previously described. As noted in FIG. 7 and 8, two front elevation shapes are provided, one such shape 48 generally adapted to be similar to the end of the user's finger.

Referring now to FIG. 9, an embodiment of the invention including a container or dispenser 56 is shown generally at 50. Contained within the container 56 is a plurality of sheets 52 which may include releasable adhesive means on at least a portion of one surface at 54. Thus, by opening lid 58 which is otherwise held closed by well-known self-closing hinges 60, the user may remove one sheet of the pad 52 at a time in the direction of the arrow for use, reclose the container 56 and store in pocket or purse.

Referring now to FIG. 11, another embodiment of the invention is shown generally at 62 formed from a single, thin, flexible sheet of paper. This embodiment 62 includes elongated band 66 having distal ends 68 and 70 and transversely extending finger cover portion 64 extending therefrom. One of the distal ends 70 of band 66 includes a releasable adhesive surface 72 such that, when the band ends 68 and 70 are wrapped around the user's finger adjacent the finger tip, the band 66 may be held thusly by the releasable adhesive surface 72. Finger cover portion 64 is then held against the finger tip for rubbing vigorously against the tooth surfaces to effect cleaning and polishing a previously described, after which, disposal of the sheet 62 is effected.

Referring to FIG. 12, a partial cross-section of another embodiment of the invention as shown at 76 formed of synthetic sponge material which is compressible to provide enhanced mateability with the irregular contours of the tooth surfaces to be cleaned. Otherwise, this embodiment of the invention, provided in sheet form, may be similar to those embodiments previously described.

Referring now to FIG. 13, another embodiment of the invention is shown generally at 74 and includes a sheet 76 of thin, flexible paper material having a generally elongated rectangular shape. In this embodiment 74, a decorative ring 78 is provided so that, when the sheet of paper 76 is held generally in the vicinity of the end of the finger F, the ring 78 may be slid over the finger F and the sheet of paper 76 in the direction of the arrow toward the first knuckle K. This ring 78 is sized somewhat smaller than a conventional ring so as not to pass over the first knuckle K but to be held there as it holds the paper sheet 76 in place against the finger F for use as previously described.

Referring lastly to FIG. 14, an alternate embodiment of the packaging and carrying arrangement of the invention is shown in roll form at 80 and includes an elongated length of paper tissue-type material which includes a plurality of transverse perforations 84. These perforations 84 thus provide a convenient line of weakness so that the user may tear individual rectangular panels 82 from the roll 80 for use as previously described.

MATERIAL SELECTION

Because of the simplicity of this novel invention, it may be fabricated of a broad range of synthetic and natural materials which have been manufactured into thin, flexible sheet form. The primary requirement for the material which comprises the invention is that at least one surface be sufficiently textured such that, when rubbed by normal finger pressure against the surfaces of the teeth, the food residue and film, daily plaque build-up and other oral acids on the teeth surfaces are removed and collected onto the sheet surface rubbed thereagainst without injuring or abrading the gums. Additionally, it is generally required that the sheet material also be generally insoluble in water and oral cavity juices such that the entire teeth surfaces may be cleaned and polished with the use of only one piece of the product.

On that basis, the invention, in its various embodiments as hereabove described, may be fabricated of a broad variety of paper products, including those which are quilted and dimpled, and may also be made of synthetic or cloth fibers, as well as synthetic foam which adds a degree to compressibility for enhanced and difficult to reach tooth surface contours. Non-poracity of the sheet material may also be desired.

Although in its most economical form, the invention will be fabricated of conventional unscented and unflavored flexible sheet paper material, the sheet material may also be impregnated with breath freshening agents and other additives for enhanced polishing and cleaning ability, as well as for enhanced anti-bacterial properties.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A disposable tooth cleaning and polishing product for manually cleaning tooth surfaces and for stimulating gums comprising:
   a single, unfolded sheet of very thin, flexible textured material having a first surface and a second surface and being substantially insoluble in water and oral cavity juices;
   said first surface textured to remove plaque, food residue, and oral cavity acids from tooth surfaces by manually rubbing said sheet material with finger pressure against the tooth surfaces;
   said second surface textured to remain in non-sliding friction contact against a user's fingertip.

2. A disposable tooth cleaning and polishing product as set forth in claim 1, wherein:
   said sheet is made of substantially non-porous material.

3. A disposable tooth cleaning and polishing product as set forth in claim 1, wherein:
   said sheet is made of cloth.

4. A disposable tooth cleaning and polishing product as set forth in claim 1, wherein:
   said sheet is made of paper.

5. A disposable tooth cleaning and polishing product as set forth in claim 4, wherein:
   said paper is textured for enhanced cleaning and polishing of tooth surfaces.

6. A disposable tooth cleaning and polishing product as set forth in claim 4, wherein:
   said paper is quilted for enhanced formability to tooth surface contours.

7. A disposable tooth cleaning and polishing product as set forth in claim 4, wherein:
   said paper id dimpled for enhanced formability to tooth surface contours.

8. A disposable tooth cleaning and polishing product as set forth in claim 1, wherein:
   said sheet is one of a plurality of said sheets each formed as part of a continuous elongated strip having periodic generally transverse perforations for facilitating detachability of each said sheet;
   said elongated strip formed into a roll for convenient carrying and dispensing.

9. A disposable tooth cleaning and polishing product as set forth in claim 1, wherein:
   said sheet is synthetic foam material for enhanced formability to tooth surfaces.

10. A disposable tooth cleaning and polishing product as set forth in claim 1, further comprising:
    a closable dispenser for containing and allowing convenient access to at least one of a plurality of said sheets within said dispenser.

11. A disposable tooth cleaning and polishing product as set forth in claim 1, further comprising:
    releasable adhesive means applied to at least a portion of said second surface to releasably adhere said sheet to a user's fingertip for use.

12. A tooth cleaning and polishing product as set forth in claim 1, wherein said sheet comprises:
    an elongated band portion having a finger cover portion extending laterally therefrom;
    said band adapted to surround a user's finger in overlapping fashion at its distal ends;
    said distal ends releasably engageable one to another for retaining said product on the user's finger during use;
    said finger cover portion adapted to lay against the user's finger end for cleaning and polishing tooth surfaces.

13. A tooth cleaning and polishing product as set forth in claim 1, wherein:
    said flexible sheet includes a breath freshener for reducing user's mouth odor.

* * * * *